(12) United States Patent
Lippert et al.

(10) Patent No.: US 11,969,726 B2
(45) Date of Patent: Apr. 30, 2024

(54) FLUID GUIDING MODULE AND FLUID GUIDING SYSTEM HAVING AT LEAST TWO FLUID GUIDING MODULES

(71) Applicant: Endress+Hauser Conducta GmbH+Co. KG, Gerlingen (DE)

(72) Inventors: Holger Lippert, Leisnig (DE); Thomas Pfauch, Leipzig (DE); Maik Thormann, Leipzig (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 959 days.

(21) Appl. No.: 16/930,312

(22) Filed: Jul. 15, 2020

(65) Prior Publication Data
US 2021/0016268 A1 Jan. 21, 2021

(30) Foreign Application Priority Data
Jul. 15, 2019 (DE) .................... 10 2019 119 078.9

(51) Int. Cl.
*G01D 11/24* (2006.01)
*B01L 3/00* (2006.01)
*G01N 1/00* (2006.01)

(52) U.S. Cl.
CPC .............. *B01L 3/502* (2013.01); *G01D 11/24* (2013.01); *G01N 2001/002* (2013.01)

(58) Field of Classification Search
CPC .................. B01L 13/502; G01D 11/24; G01N 2001/002; G01N 1/18; G01N 1/2035
USPC .......................................................... 138/108
See application file for complete search history.

(56) References Cited

U.S. PATENT DOCUMENTS

| 5,681,529 A | * | 10/1997 | Taguchi | ................. B01L 3/502 422/417 |
| 2001/0048896 A1 | | 12/2001 | Hettinger | |
| 2009/0214387 A1 | | 8/2009 | Straub et al. | |
| 2015/0377476 A1 | * | 12/2015 | Shiogama | ............ G01D 11/245 455/575.8 |

FOREIGN PATENT DOCUMENTS

| CN | 102103113 A | 6/2011 |
| DE | 19917330 A1 | 4/1999 |
| DE | 19917330 A1 | 10/2000 |
| WO | 2009024589 A1 | 2/2009 |
| WO | 2013023859 A1 | 2/2013 |
| WO | 10218606 A1 | 8/2014 |
| WO | 2014125457 A1 | 8/2014 |

* cited by examiner

*Primary Examiner* — Kelsey E Cary
(74) *Attorney, Agent, or Firm* — Kelly J. Smith; Endress+Hauser (USA) Holding, Inc.

(57) ABSTRACT

A fluid guiding module includes a housing having a sensor chamber having first and second chamber ends. The fluid guiding module includes a first connection region for connecting to a second fluid guiding module. The first connection is located on a first outer side of the housing and has a first redirection channel having first and second redirection channel ends. A chamber inlet channel fluidly couples the first redirection channel end to the first chamber end of the sensor chamber. The first redirection channel is adapted to be fluidly coupled to a chamber outlet channel of the second fluid guiding module.

9 Claims, 6 Drawing Sheets

FLUID GUIDING MODULE AND FLUID GUIDING SYSTEM HAVING AT LEAST TWO FLUID GUIDING MODULES

CROSS-REFERENCE TO RELATED APPLICATION

The present application is related to and claims the priority benefit of German Patent Application No. 10 2019 119 078.9, filed on Jul. 15, 2019, the entire contents of which are incorporated herein by reference.

TECHNICAL FIELD

The present disclosure relates to a fluid guiding module and a fluid guiding system having at least two fluid guiding modules.

BACKGROUND

In analytical measurement technology, especially in the fields of water management and environmental analysis and in industry, for example in food technology, biotechnology and pharmaceuticals, as well as for various laboratory applications, measurands, such as pH value, conductivity or the concentration of analytes, such as ions or dissolved gases, in a gaseous or liquid measurement medium are vitally important. These measurands can be detected and evaluated with sensors which have the relevant analyte sensitivities.

In order to supply the measurement medium to be analyzed to the sensors, the sensors are installed in flow-through fittings. A flow-through fitting makes it possible to stream the measurement medium against a sensor in a predetermined way. Depending on how many measurands are to be measured, one or more sensors are accommodated in a flow-through fitting. A fluid channel provided in the flow-through fitting ensures that the measurement medium to be analyzed is streamed against the sensor from a specific direction.

Flow-through fittings can be built as a multi-sensor fitting or as a fluid guiding system with a plurality of fluid guiding modules. A multi-sensor fitting makes it possible to accommodate a plurality of sensors which are arranged in different chambers of the multi-sensor fitting. The various chambers are connected to each other in such a way that a channel for guiding the fluid is formed by the multi-sensor fitting. A fluid guiding system comprises any number of fluid guiding modules, where each fluid guiding module comprises a chamber for accommodating a sensor. The fluid guiding modules are interconnected in such a way that they form a channel for guiding the fluid through all chambers of the fluid guiding system. Measurement medium must be streamed against the sensor from a specific direction depending on the sensor used in a fluid guiding module. Usually the flow against the sensor is along its axis of extent, either from top to bottom or from bottom to top.

In multi-sensor fittings, the direction of flow is predetermined by the fixedly arranged sensor chambers and fluid channels. In a fluid guiding system with fluid guiding modules, however, the direction of flow between the fluid guiding modules must change between the fluid guiding modules, depending on the sensor used in the fluid guiding module.

Known fluid guiding systems which enable redirection of the measurement medium do not have optimum sealing properties at the coupling between the two modular flow-through fittings. In addition, dead volumes can arise in the region of the redirection, increasing the risk of contaminant deposits, algae formation, etc. Furthermore, the sealing element is often not optimally placed between the two modular flow-through fittings, complicating insertion of the sealing element and compromising the service life of the sealing element.

SUMMARY

It is therefore an object of the present disclosure to provide a fluid guiding module which is simple, safe and durable.

This object is achieved according to the present disclosure by a fluid guiding module according to claim 1.

The fluid guiding module according to the present disclosure comprises:

A housing having a sensor chamber in the housing which extends along a first axis and has a first chamber end and a second chamber end axially distanced from the first chamber end, A first connection region for connecting to a second fluid guiding module, the first connection region being located on a first outer side of the housing and extending along a second axis and having a first redirection channel which extends along the second axis and has a first redirection channel end and a second redirection channel end axially distanced from the first redirection channel end, A chamber inlet channel fluidly coupling the first redirection channel end to the first chamber end of the sensor chamber, wherein the first redirection channel is adapted to be fluidly coupled to a chamber outlet channel of the second fluid guiding module, A second connection region for connecting to a third fluid guiding module, the second connection region being located on a second outer side of the housing and extending along a third axis parallel to the second axis, A chamber outlet channel fluidly coupling the second connection region to the first chamber end of the sensor chamber, wherein the chamber outlet channel is adapted to be connected to a chamber inlet channel of the third fluid guiding module, wherein the first redirection channel and/or the second redirection channel are each adapted to accommodate a sealing unit so that when the fluid guiding module is connected to the second fluid guiding module and/or the third fluid guiding module, the sealing unit is provided in each case to touch a fluid transiting between the fluid guiding module and the second fluid guiding module and/or between the fluid guiding module and the third fluid guiding module.

The fluid guiding module according to the present disclosure makes it possible for the fluid guiding module to be easily and securely connected to a further fluid guiding module. Furthermore, the fluid guiding module allows for minimization of dead volume between two connected fluid guiding modules when two fluid guiding modules are connected to each other. The fluid guiding module makes it possible to avoid excessive pinching of a seal when two fluid guiding modules are connected to each other.

In one embodiment of the present disclosure, the first connection region and the second connection region each project from the housing and are each adapted to be surrounded by a connecting element, for example, the first and second connection regions can each have a swallow-tail cross-section. This makes it possible to securely press together two fluid guiding modules that are connected to each other.

In one embodiment of the present disclosure, the second connection region has a second redirection channel extending along the third axis and having a first redirection channel end and a second redirection channel end axially distanced from the first redirection channel end. Assembly of two fluid guiding modules is simplified by two redirection channels which can be connected to one another.

In one embodiment of the present disclosure, the first redirection channel and/or the second redirection channel are formed from a circumferential side wall bounding the redirection channel and a bottom wall, wherein the bottom wall is configured as a planar surface and is adapted for receiving a sealing unit. This allows the sealing unit to not be pinched when two fluid guiding modules are connected.

The above object is also achieved by a fluid guiding system according to claim 5.

The fluid guiding system according to the present disclosure comprises:
   A first fluid guiding module according to the present disclosure,
   A second fluid guiding module according to the present disclosure,
   A sealing unit for sealing the first connection region of the first fluid guiding module to the second connection region of the second fluid guiding module,
   A connecting element for connecting the first connection region of the first fluid guiding module to the second connection region of the second fluid guiding module,
   wherein the first fluid guiding module and the second fluid guiding module are adapted to fluidly couple the chamber outlet channel of the second fluid guiding module to the chamber inlet channel of the first fluid guiding module by means of the first redirection channel of the first fluid guiding module.

The fluid guiding system enables safe and easy handling of the fluid guiding modules. Thus, depending on the field of application, any number of fluid guiding modules can be assembled into an application-specific fluid guiding system.

According to one embodiment of the present disclosure, the sealing unit comprises a sealing element and a positioning element, wherein the sealing element and the positioning element are complementary and are adapted for filling the first redirection channel or the second redirection channel in such a way that the sealing element is positioned by the positioning element in the first redirection channel or in the second redirection channel such that the sealing element is aligned with the chamber inlet channel or the chamber outlet channel. Thus, a dead volume between two fluid guiding modules is minimized if redirection of the measurement medium is not desired.

In one embodiment of the present disclosure, the sealing unit comprises a first section having an opening and a second section, wherein the first section and the second section are arranged such that when the sealing unit is inserted into the first redirection channel or the second redirection channel, the opening is adapted to align with the chamber inlet channel or the chamber outlet channel. Thus, a dead volume between two fluid guiding modules is minimized if redirection of the measurement medium is not desired.

In one embodiment of the present disclosure, the sealing unit has a sealing lip and a redirection opening, wherein the sealing lip is designed such that the sealing lip extends from the first redirection channel end to the second redirection channel end when the sealing unit is arranged in the first redirection channel or in the second redirection channel. Thus, a dead volume between two fluid guiding modules is minimized if a redirection of the measurement medium is desired.

In one embodiment of the present disclosure, the sealing unit has a sealing rim which extends around the redirection opening. The sealing rim makes it possible to save material when producing the sealing unit.

In one embodiment of the present disclosure, the first and second connection regions of the first fluid guiding module and the second fluid guiding module each have a swallowtail cross-section and the connecting element has a shape complementary to the connection regions. Thus, a secure connection between two fluid guiding modules to be connected is achieved.

The present disclosure is explained in more detail on the basis of the following description of the figures. They show.

Figure 1:
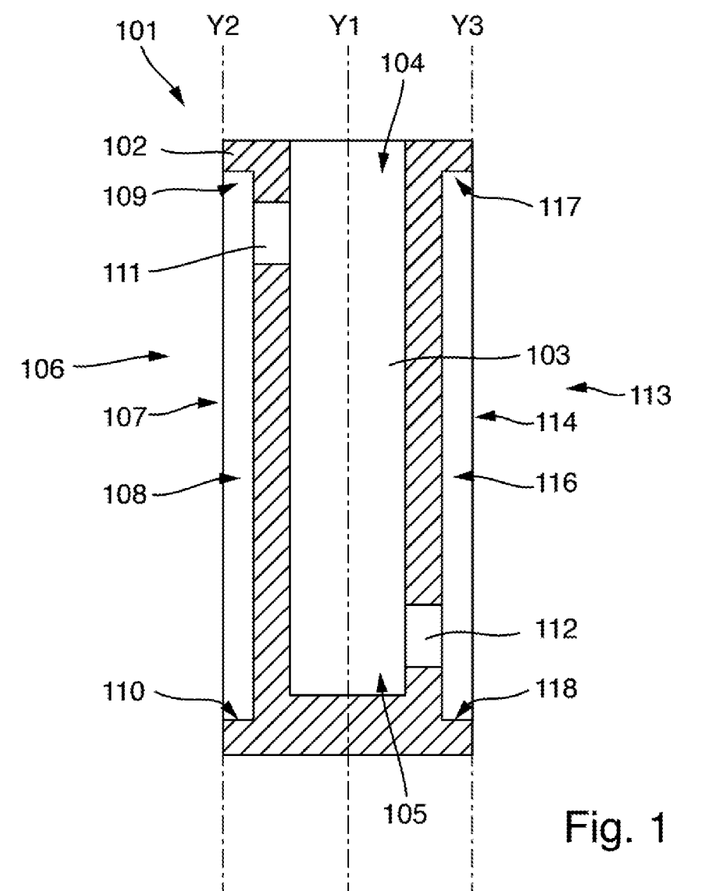
FIG. 1: a longitudinal section with a schematic illustration of a fluid guiding module according to the present disclosure.

FIG. 1 shows a fluid guiding module 101 having a housing 102. In the housing 102, there is a sensor chamber 103 which extends along a first axis Y1. The sensor chamber 103 has a first chamber end 104 and a second chamber end 105 axially distanced from the first chamber end 104. The sensor chamber 103 has a sensor inlet and is adapted to receive a sensor through the sensor inlet. The sensor is introduced into the sensor chamber 103 from above along the axis Y1. For example, sensor chamber 103 is adapted to receive a pH sensor, a redox sensor, a flow rate sensor, or a chlorine sensor.

The fluid guiding module 101 has a first connection region 106 for connecting to a second fluid guiding module 201 or a third fluid guiding module 301.

The second fluid guiding module 201 and the third fluid guiding module 301 are identical to the fluid guiding module 101, which is called first fluid guiding module 101 in the following for the sake of simplicity. That is, the second and third fluid guiding modules 201, 301 have the same features as the first fluid guiding module 101. All the following features introduced with respect to the first fluid guiding module 101 are thus also considered introduced with respect to the second and third fluid guiding modules 201, 301. The reference numerals for features of the second fluid guiding module 201 have a two in the hundreds place and the reference numerals for features of the third fluid guiding module 301 have a three in the hundreds place. The tens and ones of the reference numerals for the features of the fluid guiding modules 101, 201, 301 are identical.

The first connection region 106 is located on a first outer side 107 of the housing 102 and extends along a second axis Y2. The first connection region 106 has a first redirection channel 108 which extends along the second axis Y2. Redirection channel 108 has a first redirection channel end 109 and a second redirection channel end 110 axially distanced from first redirection channel end 109.

The fluid guiding module 101 comprises a chamber inlet channel 111 fluidly coupling the first redirection channel end 109 to the first chamber end 104 of the sensor chamber 103. The first redirection channel 108 is adapted to be fluidly connected to a chamber outlet channel 212 of the second fluid guiding module 201.

The fluid guiding module 101 has a second connection region 113 for connecting to the third fluid guiding module 301. The second connection region 113 is located on a second outer side 114 of the housing 102 and extends along a third axis Y3 parallel to the second axis Y2.

The fluid guiding module 101 comprises a chamber outlet channel 112 fluidly coupling the second connection region 113 to the first chamber end 104 of the sensor chamber 103. The chamber outlet channel 112 is adapted to be connected to a chamber inlet channel 311 of the third fluid guiding module 301.

Figure 4:
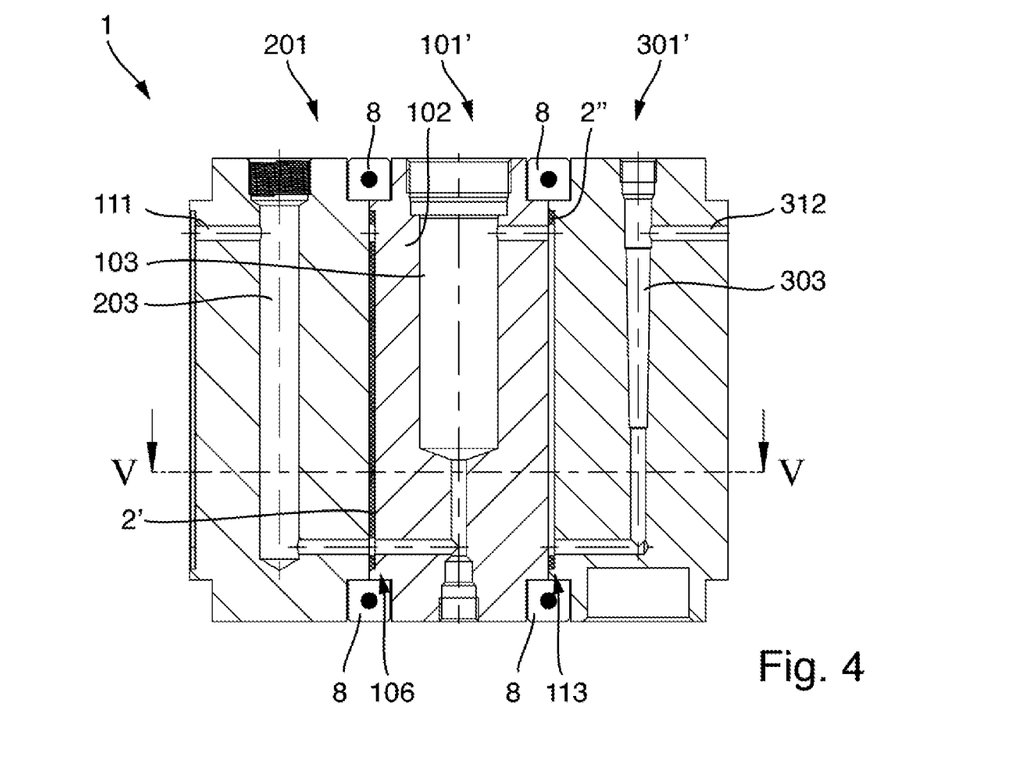
FIG. 4: a longitudinal section through a fluid guiding system according to the present disclosure.

In an alternative embodiment of the fluid guiding module 101', the chamber inlet channel 111 fluidly connects the second redirection channel end 110 to the second chamber end 105 of the sensor chamber 103 (see middle fluid guiding module 101' and right-hand fluid guiding module 301' in FIG. 4). In this embodiment, the chamber outlet channel 112 fluidly connects the first chamber end 104 of the sensor chamber 103 to the second connection region 113 (see middle fluid guiding module 101' and right-hand fluid guiding module 301' in FIG. 4).

In the fluid guiding module 101 shown in FIG. 1, the second connection region 113 has a second redirection channel 116. The second redirection channel 116 extends along the third axis Y3 and has a first redirection channel end 117 and a second redirection channel end 118 axially distanced from the first redirection channel end 117. In this embodiment, the first redirection channel 108 and the second redirection channel 116 are each adapted to receive half of a sealing unit 2.

Figure 2:
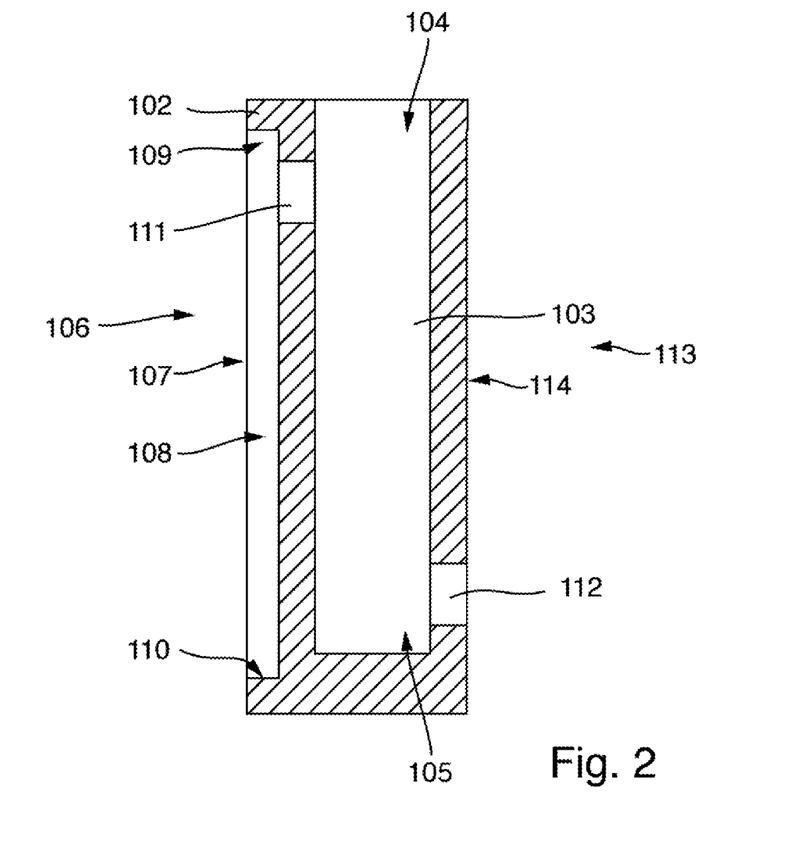
FIG. 2: a longitudinal section with a schematic illustration of an embodiment of the fluid guiding module according to the present disclosure.

In contrast, in the fluid guiding module 101 shown in FIG. 2, the second connection region 113 does not have a second redirection channel 116. In this embodiment, however, the first redirection channel 108 is formed deeper in the housing 102 with respect to the first outer side 107 in order to receive the sealing unit 2 by itself. The fluid guiding modules 101', 201, 301' shown in FIGS. 4 and 5 have a first redirection channel 108, 208, 308 and a second redirection channel 116, 216, 316.

Figure 3:
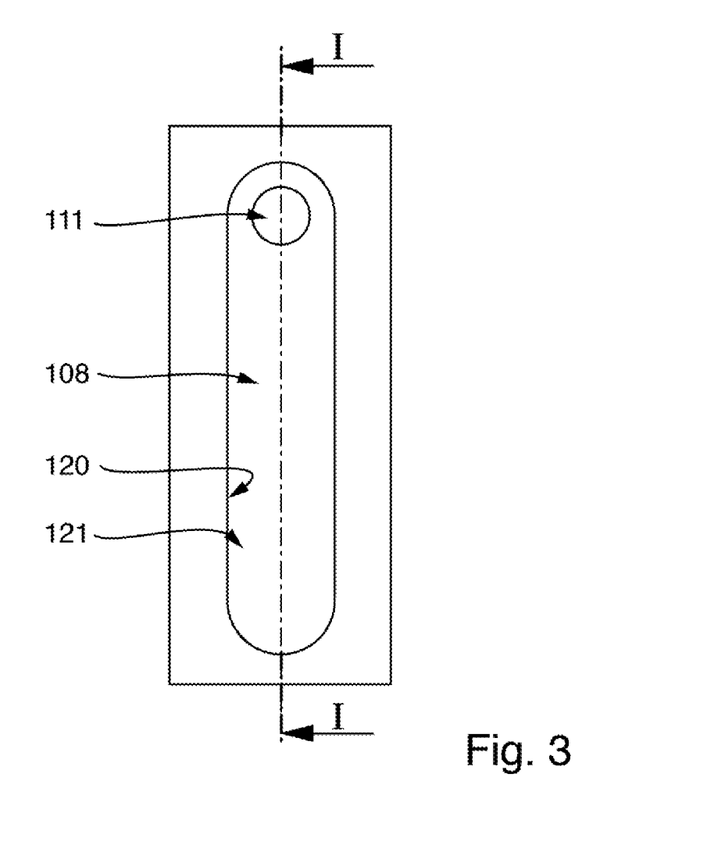
FIG. 3: a side view with a schematic illustration of the fluid guiding module from FIG. 1.

FIG. 3 shows a side view of the fluid guiding module 101 with a detailed illustration of the first redirection channel 108. The first redirection channel 108 is defined by a circumferential side wall 120 bounding the first redirection channel 108 and by a bottom wall 121. The bottom wall 121 is configured as a planar surface and is adapted to receive the sealing unit 2. The bottom wall 121 is advantageously flat, i.e. it has no unevennesses and no groove. This prevents deposits on the bottom wall 121. The bottom wall 121 advantageously directly abuts the side wall 120 bounding the first redirection channel 108. The second redirection channel 116 may be formed like the first redirection channel 108.

The first redirection channel 108 allows accommodation of the sealing unit 2, which extends along the side wall 120 and can deform inwards into the first redirection channel 108 from the side wall 120. Thus, when two fluid guiding modules are connected and sealed by the sealing unit 2, the sealing unit 2 will not be pinched in a damaging manner. The side wall 120 is advantageously flat, i.e. it has no unevennesses and no groove. This prevents deposits on the side wall 120.

FIG. 4 shows a fluid guiding system 1 with the first fluid guiding module 101', second fluid guiding module 201 and third fluid guiding module 301' arranged in series. Arranged in series here means that the chamber outlet channels 212, 112 are fluidly coupled to the corresponding chamber inlet channels 111, 311. Thus, a system channel extending from the chamber inlet channel 211 to the chamber outlet channel 312 through the fluid guiding modules 101', 201, 301' and thus through the fluid guiding system 1 is formed. The system channel comprises the chamber inlet channels 211, 111, 311, the sensor chambers 203, 103, 303, the chamber outlet channels 212, 112, 312, the first redirection channels 208, 108, 308 and, optionally, the second redirection channels 216, 116, 316, which are present in the embodiment of the fluid guiding modules illustrated in FIG. 4.

A sealing unit 2 is arranged in each case between the second fluid guiding module 201, the first fluid guiding module 101' and the third fluid guiding module 301'. The sealing unit 2 is adapted for sealing the two adjacent fluid guiding modules so that no measurement medium can escape to the outside. "To the outside" here means outside the system channel of the fluid guiding system 1. Of course, if fewer or more than three fluid guiding modules are used in the fluid guiding system, a sealing unit 2 is arranged between each fluid guiding module.

The fluid guiding system 1 allows two side-by-side fluid guiding modules 101', 201, 301' to be adapted to collectively form a redirection channel that is closed towards the outside by means of the second redirection channel 116 of the first fluid guiding module 101' and the first redirection channel 108 of the third fluid guiding module 301'.

Figure 5:
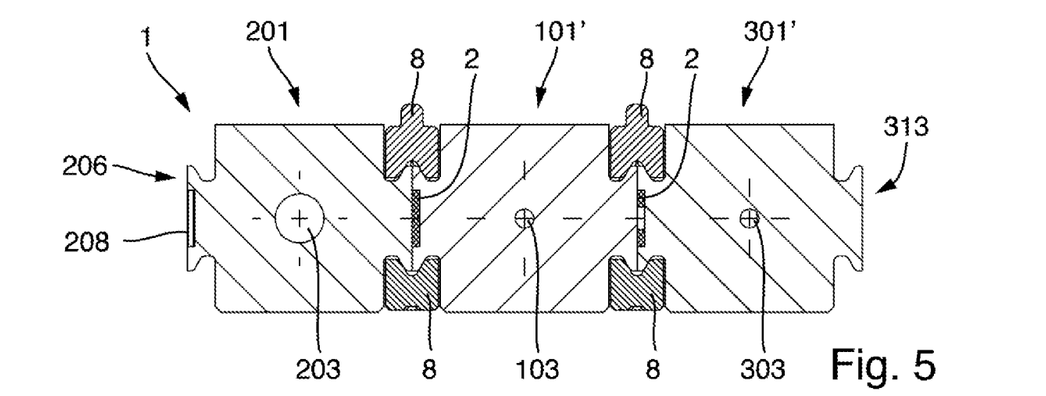
FIG. 5: a cross-section through the fluid guiding system from FIG. 4.

In the fluid guiding modules 101', 201, 301' illustrated in FIG. 4 and FIG. 5, the first connection region 206, 106, 306 and the second connection region 213, 113, 313 each project from the housing 202, 102, 302. The first connection region 106 and the second connection region 113 are adapted to be surrounded by a connecting element 8. For example, the first and second connection regions 106, 113 each have a swallow-tail cross-section (see FIG. 5). The first and second connection regions 106, 113 may also have other cross-sectional shapes suitable for pressing together the fluid guiding modules connected by the connecting element 8.

The connecting element 8 has a cross-section which is complementary to the swallow-tail cross-section of the first and second connection regions 106, 113 (see FIG. 5). Thus, the connecting element 8 is adapted for pressing together the first connection region 106 of the first fluid guiding module 101 and the second connection region 213 of the second fluid guiding module 201, as well as for pressing together the second connection region 113 of the first fluid guiding module 101' and the first connection region 306 of the third fluid guiding module 301', as shown in FIG. 5.

The connecting element 8 is, for example, embodied in two parts. In this case, the two parts of the connecting element 8 are adapted for being connected to one another by a tensioning element, for example a screw (not shown).

Figure 6:
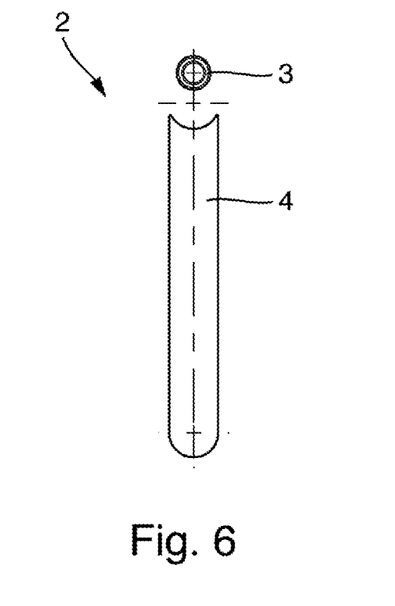
FIG. 6: a sealing unit.

FIG. 6 shows an embodiment of the sealing unit 2. In this embodiment, the sealing unit 2 comprises a sealing element 3 and a positioning element 4. The sealing element 3 is, for example, an O-ring. The sealing element 3 is, for example, made of rubber. The positioning element 4 is, for example, a plastic element. The positioning element 4 allows the O-ring to not slip. Thus, the sealing element 3 remains positioned in the fluid guiding system 1 between the chamber outlet channel and the chamber inlet channel of two fluid guiding modules. The positioning element 4 and the O-ring are designed in such a way that the first and/or second redirection channel of the fluid guiding module is filled by the positioning element 4 and the O-ring. The positioning element 4 also allows an "unneeded" redirection channel to be filled in order to reduce dead volume in the fluid guiding system 1. The redirection channel is "unneeded" if, as shown in FIG. 4, the chamber outlet channel 212 of the second fluid guiding module 201 is aligned with the chamber inlet channel 111 of the first fluid guiding module 101', i.e. can be directly connected by a sealing element 3 without redirection of the measurement medium. In other words, in this case, no redirection of the measurement medium takes place.

Figure 7:
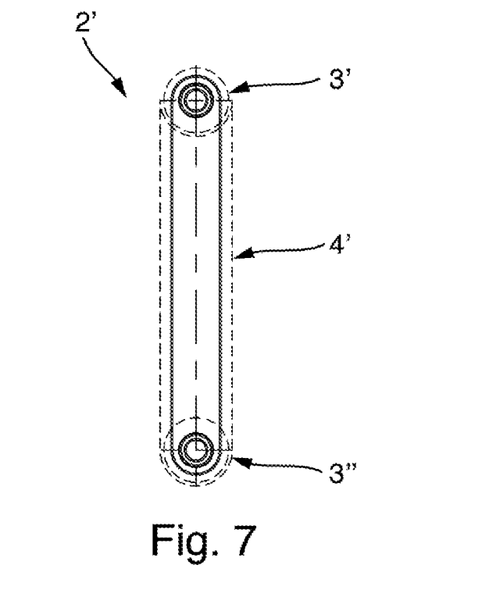
FIG. 7: another embodiment of the sealing unit.

FIG. 7 shows an alternative embodiment of the sealing unit 2'. In this embodiment, the sealing unit 2' is integrally formed. The sealing unit 2' is, for example, made of rubber. The sealing unit 2' has a first section 3' with an opening and a second section 4'. The first section 3' is adapted for sealing the chamber outlet channel 212 of the second fluid guiding module 201 with the chamber inlet channel 111 of the first fluid guiding module 101, 101' (see also FIG. 4). The second section 4' is adapted for filling the first and/or second redirection channel of the fluid guiding module (see also FIG. 4). The second section 4' thus enables the first section 3' to be positioned in the first and/or second redirection channel so that the opening is aligned with the chamber outlet channel and the chamber inlet channel of the two fluid guiding modules to be connected, as well as reducing dead volume in the first and/or second redirection channel. As shown in FIG. 7, the second section 4' optionally has a third section 3" with an opening. The third section 3" is identical to the first section 3'. The third section 3" makes it easier for a user to assemble the fluid guiding system 1, since the orientation of the sealing unit 2" need not be considered. In other words, the sealing unit 2" guarantees that, in a fluid guiding system 1 having a chamber outlet channel 111 aligned with a chamber inlet channel 211, a section 3', 3" is always positioned with an opening aligned between the chamber inlet channel 211 and the chamber outlet channel 111.

Figure 8:
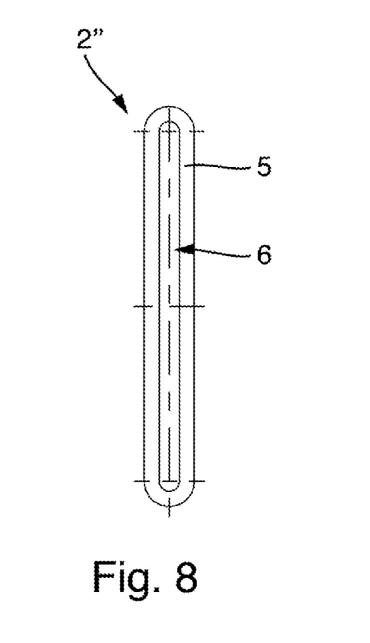
FIG. 8: an alternative embodiment of the sealing unit.

FIG. 8 shows a further alternative embodiment of the sealing unit 2". The sealing unit 2" has a sealing lip 5 and a redirection opening 6. The sealing lip 5 is adapted for sealing the chamber outlet channel 112 of the first fluid guiding module 201 with the chamber inlet channel 311 of the third fluid guiding module 301, 301' (see also FIGS. 4 and 5). The redirection opening 6 is adapted for redirecting the measurement medium from the chamber outlet channel 112 of the first fluid guiding module 201 to the chamber inlet channel 311 of the third fluid guiding module 301, 301'. Redirection here means a change from the first redirection channel end 117, 217 of the second redirection channel 116 of the fluid guiding module 101', 201 to the second redirection channel end 110, 310 of the first redirection channel 108, 308 of the fluid guiding module 101', 301' (partially illustrated in FIG. 4) or a change from the second redirection channel end 118, 218 of the second redirection channel 116 of a fluid guiding module 101, 201 to the first redirection channel end 109, 309 of the first redirection channel 108, 308 of the fluid guiding module 101, 301 (not shown).

Figure 9:
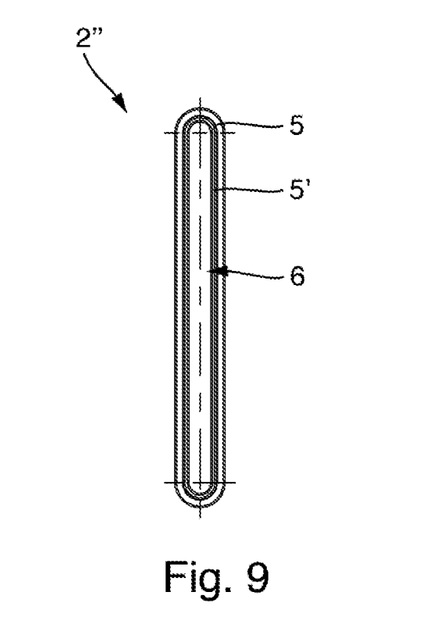
FIG. 9: a further embodiment of the sealing unit from FIG. 8.

FIG. 9 shows the sealing unit 2" with a sealing rim 5'. The sealing unit 2" is made of rubber, for example. The sealing rim 5' extends around the redirection opening 6. The sealing rim 5' is formed to be adapted to come into contact with the bottom wall 121 of the redirection channel 108, 116. The sealing rim 5' is designed not to come into contact with the side wall 120 of the redirection channel 108, 116. The sealing rim 5' is lamellar. The sealing rim 5' allows material to be saved when producing the sealing unit 2".

Figure 10:
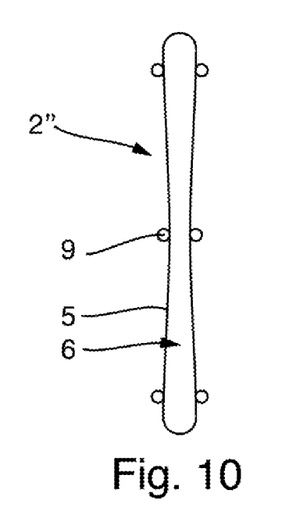
FIG. 10: a further embodiment of the sealing unit from FIG. 8.
Figure 11:
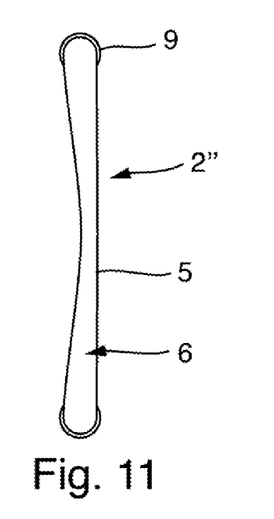
FIG. 11: a further embodiment of the sealing unit from FIG. 8.

FIG. 10 and FIG. 11 show an embodiment of the sealing unit 2" with at least one retaining button 9 arranged on the sealing lip 5. The retaining button 9 is preferably arranged such that it does not project into the redirection opening 6. For example, as shown in FIG. 10, a plurality of retaining buttons are circumferentially arranged on an outer edge of the sealing lip 5. Alternatively, as shown in FIG. 11, a retaining button 9 is arranged at each end of the sealing unit 2". The retaining button 9 is adapted to be received by a complementary opening in the fluid guiding module 101, 201, 301. The retaining button 9 has the advantage that the sealing lip 5 of the sealing unit 2" is held stably in the fluid guiding module 101, 201, 301, more precisely in the redirection channel of the fluid guiding module.

Figure 12:
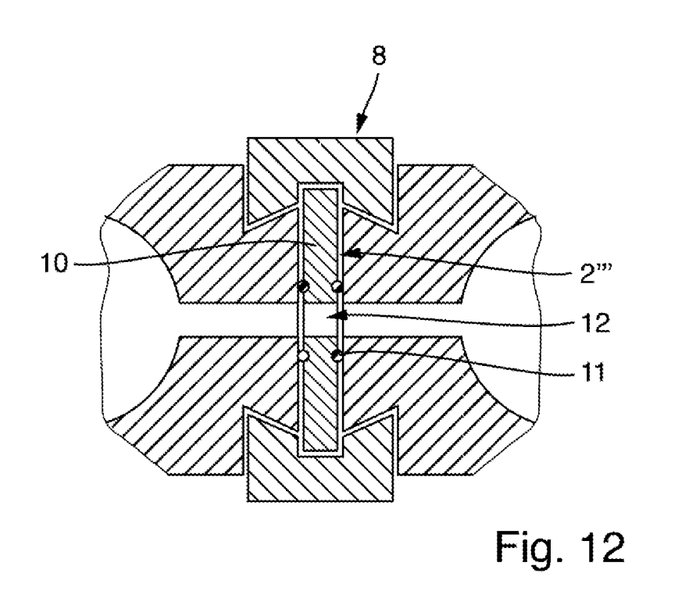
FIG. 12: a schematic illustration of a further alternative embodiment of the sealing unit.

FIG. 12 shows an alternative sealing unit 2''' with a sealing plate 10, a sealing thread 11 and a through-hole 12 arranged in the sealing plate 10. The through-hole 12 is arranged such that when the sealing unit 2''' is positioned between two fluid guiding modules 101, 201, 301, the chamber outlet channel of a fluid guiding module is connected to the chamber inlet channel of another fluid guiding module. The connecting element 8 is adapted for fixing in place the sealing unit 2''' as well as the two fluid guiding modules to be connected. The sealing thread 11 runs around the through-hole. In this way, the sealing unit 2''' is connected to the fluid guiding module in a leak-proof manner. An advantage of the sealing unit 2''' is that it is easy to mount in the fluid guiding system 1.

Depending on the design of the fluid guiding module, i.e. depending on whether a chamber inlet channel 111, 211, 311 opens into the first redirection channel end 109, 209, 309 or into the second redirection channel end 110, 210, 310 of the first redirection channel 108, 208, 308 and/or depending on whether a chamber outlet channel 112, 212, 312 opens into the first redirection channel end 117, 217, 317 or into the second redirection channel end 118, 218, 318 of the second redirection channel 116, 216, 316 and thus whether the measurement medium in the fluid guiding system 1 is intended to be redirected between two successive fluid guiding modules 101, 201, 301 or not, the sealing unit 2, 2' or the sealing unit 2", 2''' is used between the successively arranged fluid guiding modules 101, 201, 301.

Use of the sealing unit 2, 2', 2", 2''' in the fluid guiding system 1 has the advantage that the fluid guiding modules 101, 201, 301 can be connected in a leak-proof and space-saving manner. The sealing unit 2" thus makes it possible, especially if a redirection is to be implemented between two fluid guiding modules, not to place an additional space-requiring redirecting component between the fluid guiding modules.

An advantage of the fluid guiding module 101, 201, 301 is that the sealing unit 2, 2', 2", 2''' is not exposed to shearing when the fluid guiding modules 101, 201, 301 are joined together. This is of particular importance above all when the sealing unit comprises an elastic material, such as rubber. As can be seen in FIG. 3, the first redirection channel 108, 208, 308 and/or second redirection channel 116, 216, 316 is designed such that the sealing unit 2, 2', 2", 2''' is expandable into the center of the first redirection channel 108, 208, 308 and/or of the second redirection channel 116, 216, 316. As can also be seen in FIG. 3, the first redirection channel 108, 208, 308 and/or second redirection channel 116, 216, 316 has a region surrounding the chamber inlet channel 111, 211, 311 and/or the chamber outlet channel 112, 212, 312, which is bounded by the side wall 120 and is adapted for receiving the sealing unit 2, 2', 2", 2'". The circumferential region is preferably planar. In other words, the circumferential region is open for an expansion of the sealing unit inwards, that is to say, in the direction of the chamber inlet channel 111, 211, 311 and/or of the chamber outlet channel 112, 212, 312, and/or does not limit expansion of the sealing unit inwards.

The invention claimed is:

1. A fluid guiding module, comprising
a housing having a sensor chamber in the housing which extends along a first axis and has a first chamber end and a second chamber end axially distanced from the first chamber end,
a first connection region for connecting to a second fluid guiding module, the first connection region being located on a first outer side of the housing and extending along a second axis and having a first redirection channel which extends along the second axis and has a first redirection channel end and a second redirection channel end axially distanced from the first redirection channel end along the first redirection channel,
a chamber inlet channel fluidly coupling the first redirection channel end to the first chamber end of the sensor chamber,
wherein the first redirection channel is adapted to be fluidly coupled to a chamber outlet channel of the second fluid guiding module,
a second connection region for connecting to a third fluid guiding module, the second connection region being located on a second outer side of the housing and extending along a third axis parallel to the second axis,
a chamber outlet channel fluidly coupling the second connection region to the first chamber end of the sensor chamber,
wherein the chamber outlet channel is adapted to be connected to a chamber inlet channel of the third fluid guiding module,
wherein the first redirection channel and/or a second redirection channel are each adapted to accommodate a sealing unit so that when the fluid guiding module is connected to the second fluid guiding module and/or the third fluid guiding module, the sealing unit is provided in each case to touch a fluid transiting between the fluid guiding module and the second fluid guiding module and/or between the fluid guiding module and the third fluid guiding module;
wherein the first redirection channel and/or the second redirection channel are formed from a circumferential side wall bounding the redirection channel and a bottom wall, wherein the bottom wall is configured as a planar surface and is adapted for receiving the sealing unit.

2. The fluid guiding module according to claim 1, wherein the first connection region and the second connection region each project from the housing and are adapted to be surrounded by a connecting element, wherein the connecting element is configured to press together the first and second connection regions.

3. The fluid guiding module according to claim 1, wherein the second connection region comprises the second redirection channel extending along the third axis and having the first redirection channel end and the second redirection channel end axially distanced from the first redirection channel end.

4. A fluid guiding system comprising,
first and second fluid guiding modules, including:
a housing having a sensor chamber in the housing which extends along a first axis and has a first chamber end and a second chamber end axially distanced from the first chamber end,
a first connection region for connecting to a second fluid guiding module, the first connection region being located on a first outer side of the housing and extending along a second axis and having a first redirection channel which extends along the second axis and has a first redirection channel end and a second redirection channel end axially distanced from the first redirection channel end along the first redirection channel,
a chamber inlet channel fluidly coupling the first redirection channel end to the first chamber end of the sensor chamber,
wherein the first redirection channel is adapted to be fluidly coupled to a chamber outlet channel of the second fluid guiding module,
a second connection region for connecting to a third fluid guiding module, the second connection region being located on a second outer side of the housing and extending along a third axis parallel to the second axis,
a chamber outlet channel fluidly coupling the second connection region to the first chamber end of the sensor chamber,
wherein the chamber outlet channel is adapted to be connected to a chamber inlet channel of the third fluid guiding module,
wherein the first redirection channel and/or the second redirection channel are each adapted to accommodate a sealing unit so that when the fluid guiding module is connected to the second fluid guiding module and/or the third fluid guiding module, the sealing unit is provided in each case to touch a fluid transiting between the fluid guiding module and the second fluid guiding module and/or between the fluid guiding module and the third fluid guiding module;
the sealing unit for sealing the first connection region of the first fluid guiding module to the of the second fluid guiding module,
a connecting element for connecting the first connection region of the first fluid guiding module to the second connection region,
wherein the first fluid guiding module and the second fluid guiding module are adapted to fluidly couple the chamber outlet channel of the second fluid guiding module to the chamber inlet channel of the first fluid guiding module by means of the first redirection channel of the first fluid guiding module,
wherein the connecting element is configured to press together the first and second connection regions;
wherein the first redirection channel and/or a second redirection channel are formed from a circumferential side wall bounding the redirection channel and a bottom wall, wherein the bottom wall is configured as a planar surface and is adapted for receiving the sealing unit.

5. The fluid guiding system according to claim 4, wherein the sealing unit comprises a sealing element and a positioning element, wherein the sealing element and the positioning element are configured to be complementary and adapted for filling the first redirection channel or the second redirection channel in such a way that the sealing element is positioned by the positioning element in the first redirection channel or in the second redirection channel such that the sealing element is aligned with the chamber inlet channel or the chamber outlet channel.

6. The fluid guiding system according claim 4, wherein the sealing unit comprises a first section having an opening and a second section, wherein the first section and the second section are arranged such that when the sealing unit is inserted into the first redirection channel or the second redirection channel, the opening is adapted to align with the chamber inlet channel or the chamber outlet channel.

7. The fluid guiding system according to claim 4, wherein the sealing unit has a sealing lip and a redirection opening, wherein the sealing lip is designed such that the sealing lip extends from the first redirection channel end to the second redirection channel end when the sealing unit is arranged in the first redirection channel or in the second redirection channel.

8. The fluid guiding system according to claim 7, wherein the sealing unit has a sealing rim extending around the redirection opening.

9. The fluid guiding system according to claim 4, wherein the connecting element has a shape complementary to the connection regions.

* * * * *